United States Patent
Da Silva

(10) Patent No.: US 9,636,295 B2
(45) Date of Patent: May 2, 2017

(54) COSMETIC COMPOSITIONS, METHOD FOR PREPARING A COSMETIC COMPOSITION, COSMETIC USE OF THE COMPOSITION AND COSMETIC METHOD FOR STRAIGHTENING AND/OR SHAPING KERATINOUS MATERIALS

(71) Applicant: Guilherme Beltrão De Almeida, Curitiba (BR)

(72) Inventor: Idrozina Oliveira Da Silva, Curitiba (BR)

(73) Assignee: GUILHERME BELTRÃO DE ALMEIDA (BR)

( * ) Notice: Subject to any disclaimer, the term of this patent is extended or adjusted under 35 U.S.C. 154(b) by 0 days.

(21) Appl. No.: 14/352,485

(22) PCT Filed: Oct. 19, 2012

(86) PCT No.: PCT/BR2012/000411
§ 371 (c)(1),
(2) Date: Apr. 17, 2014

(87) PCT Pub. No.: WO2013/056332
PCT Pub. Date: Apr. 25, 2013

(65) Prior Publication Data
US 2014/0242017 A1 Aug. 28, 2014

(30) Foreign Application Priority Data
Oct. 19, 2011 (BR) .............. PI 11104321-0

(51) Int. Cl.
| | | |
|---|---|---|
| A61K 8/96 | (2006.01) |
| A61K 8/97 | (2006.01) |
| A61K 8/72 | (2006.01) |
| A61K 8/58 | (2006.01) |
| A61K 8/34 | (2006.01) |
| A61K 8/36 | (2006.01) |
| A61K 8/73 | (2006.01) |
| A61K 8/19 | (2006.01) |
| A61K 8/37 | (2006.01) |
| A61Q 5/06 | (2006.01) |
| A61Q 5/00 | (2006.01) |
| A61Q 5/12 | (2006.01) |

(52) U.S. Cl.
CPC .................. *A61K 8/97* (2013.01); *A61K 8/19* (2013.01); *A61K 8/345* (2013.01); *A61K 8/361* (2013.01); *A61K 8/375* (2013.01); *A61K 8/585* (2013.01); *A61K 8/72* (2013.01); *A61K 8/731* (2013.01); *A61K 8/96* (2013.01); *A61Q 5/00* (2013.01); *A61Q 5/06* (2013.01); *A61Q 5/12* (2013.01)

(58) Field of Classification Search
CPC .......... A61K 8/19; A61K 8/345; A61K 8/361; A61K 8/375; A61K 8/585; A61K 8/72; A61K 8/731; A61K 8/96; A61K 8/97; A61Q 5/00; A61Q 5/06; A61Q 5/12
See application file for complete search history.

(56) References Cited

U.S. PATENT DOCUMENTS

| | | | |
|---|---|---|---|
| 5,512,276 A | * | 4/1996 | Lang ................ A61K 8/72 424/401 |
| 7,829,514 B2 | | 11/2010 | Paul et al. |
| 2004/0208843 A1 | | 10/2004 | Bernard et al. |
| 2005/0112155 A1 | | 5/2005 | Giroud et al. |
| 2009/0048132 A1 | | 2/2009 | Paul et al. |

OTHER PUBLICATIONS

International search report of PCT/BR2012/000411 mailed Feb. 17, 2013.

* cited by examiner

*Primary Examiner* — Aradhana Sasan
(74) *Attorney, Agent, or Firm* — Dilworth IP LLC

(57) ABSTRACT

The present invention relates to a new cosmetic product for treating keratinous materials, particularly hair, to the method for preparing the cosmetic product, and to a cosmetic method for the care of keratinous material using these compositions.

34 Claims, No Drawings

COSMETIC COMPOSITIONS, METHOD FOR PREPARING A COSMETIC COMPOSITION, COSMETIC USE OF THE COMPOSITION AND COSMETIC METHOD FOR STRAIGHTENING AND/OR SHAPING KERATINOUS MATERIALS

This application is a U.S. National Phase Application under 35 U.S.C. §371 of International Patent Application No. PCT/BR2012/000411, filed on Oct. 19, 2012, which claims priority to Brazilian Patent Application No. PI 1104321-0, filed on Oct. 19, 2011, the disclosures of each of which are incorporated herein by reference in their entirety.

FIELD OF THE INVENTION

The present invention refers to a new cosmetic composition for straightening or modeling of keratinous materials, particularly keratinous fibers, and more preferably hair. Further, the present invention refers to the process for the preparation of said composition and to a cosmetic process of keratinous material care that uses said composition.

BACKGROUND OF THE INVENTION

Human hair is made up of proteins, and the structure and modeling thereof are guaranteed by disulfide bridges between the amino acids of the polypeptide chain. These bridges are covalent bonds that may be disrupted in extreme pH conditions. From the disruption of these bonds it is then possible to shape the hair strand as desired (straighten or curl).

The disruption of disulfide bridges can be carried out with substances that modify the pH in an extreme way, such as, for example, hydroxides. However, the use of such substances leaves the hair dehydrated, with open scales, thus, in need of a conditioning agent to restore its normal structure.

In this sense, there is a constant search for cosmetic compositions which are capable of shaping or straightening keratinous fibers, particularly the hair, but without damaging the strands, which are atoxic, of easy application and maintenance.

*Eucalyptus* ashes contain alkaline and alkaline earth minerals in the presence of carbonates that, when in solution, ensure the property of keeping the pH high. This solution, when applied to the hair strand, acts by disrupting the disulfide bonds, thus enabling the realization of a new hair modeling.

It is known in the prior art that only these ashes in solution are able to shape the hair, however, at the same time they are aggressive to the hair strand, rendering it weak, opaque and brittle.

Currently, modeling or straightening procedures of keratinous fibers are carried out by the use of plasticizer products, natural and synthetic resins, as well as formaldehyde, cysteine and other derivatives of sulfur, in addition to glutaraldehyde, hydrogen peroxide, ammonium thioglycolate, quaternary ammonium compounds and pH altering substances, all applied in isolation or through combinations among them.

Most commonly used products are products based on formaldehyde (formalin), which is a chemical compound capable of altering the structure of the hair strand. However, its use is restricted due to the fact that it is a carcinogenic compound. In addition, its application requires caution so that it does not harm the hair strand, the scalp, or the health of the human being.

Thus, the present invention aims to solve the problems mentioned above, providing a new cosmetic composition for straightening or modeling keratinous fibers, particularly the hair, which does not present the drawbacks found in the prior art.

SUMMARY OF THE INVENTION

The present invention is intended to change the configuration of keratinous materials, both for straightening and modeling of such fibers. Keratinous materials treated with the composition of the present invention may be preceded and/or followed by other chemical processes, such as dyeing and discoloration, without which the materials are damaged.

Thus, the present invention refers to a cosmetic composition for straightening or modeling keratinous materials, particularly keratinous fibers, comprising: i) from 0.001 to 30% of calcium salts; ii) from 1 to 20% of cellulose or derivatives thereof; iii) from 1 to 10% of lignin; iv) from 1 to 10% of fatty acids; v) from 0 to 10% of triglycerides; vi) from 0 to 10% of glycerin; and water.

In a further aspect, the present invention relates to a process for the preparation of the cosmetic composition of the present invention through percolation of ashes and a homogeneous paste of avocado, in alternating layers, in a container that allows outflow of an extractor liquid through the layers and withdrawal of the percolation product through the bottom of the container. Preferably, the extractor liquid used in the percolation of the present invention is water.

The present invention further aims at a composition obtained by the process described herein, and use of such composition for straightening and/or modeling keratinous materials, particularly hair.

Further, another achievement of the present invention refers to a cosmetic process for straightening and/or modeling keratinous materials, in particular hair, comprising applying a composition according to the present invention on keratinous materials.

DETAILED DESCRIPTION OF THE INVENTION

According to one embodiment, the present invention refers to a cosmetic composition for straightening or modeling keratinous materials, comprising: i) from 0.001 to 30% of calcium salts; ii) from 1 to 20% of cellulose or derivatives thereof; iii) from 1 to 10% of lignin; iv) from 1 to 10% of fatty acids; v) from 0 to 10% of triglycerides; vi) from 0 to 10% of glycerin; and water.

Particularly, a composition of the present invention comprises: i) from 0.001 to 5% of calcium salts; ii) from 1 to 10% of cellulose or derivatives thereof; iii) from 1 to 5% of lignin; iv) from 2 to 6% of fatty acids; v) from 0 to 2% of triglycerides; vi) from 0 to 2% of glycerin; and water.

In a preferred embodiment, the composition of the present invention comprises: i) 0.002% of calcium salts; ii) 6.6% of cellulose or derivatives thereof; iii) 1.2% of lignin; iv) 4.8% of fatty acids; v) 0% of triglycerides; vi) from 0% of glycerin; and water.

According to the present invention, keratinous materials of greatest interest are keratinous fibers, more particularly hair.

Cellulose, lignin, fatty acids, triglycerides and glycerine derivatives present in the composition of this invention are from various sources, both of animal and vegetable origin, by grinding or maceration of fruit, or parts thereof, which somehow generates the elements described above.

The fatty acids that may be present in the composition described here include saturated, monounsaturated and/or polyunsaturated fatty acids. Particularly, oleic, linoleic, stearic and palmitic acids are present in the composition of this invention. Particularly, the fatty acids present in the composition of this invention are selected from one or more of cyclopentatridecanoic acid, hexadecenoic acid, hexadecanoic acid, octadecenoic acid and/or octadecanoic acid.

In a preferred embodiment of the present invention, the composition described here further comprises siloxane compounds.

Particularly, the siloxane compounds present in the composition according to the present invention are selected from one or more of dodecamethyl cyclohexasiloxane, ethoxy hexamethyl tris(trimetilsiloxy)tetrassiloxane, isopropoxy hexamethyl tris(trimetilsiloxy)tetrasiloxane, and/or butoxy hexamethyl tris(trimetilsiloxy)tetrasiloxane.

The composition of the present invention can be applied to the hair for varying periods, cold or hot, through usual procedures used in establishments intended for this purpose, being free of formaldehydes and other substances that damage the hair and have their contents governed by the relevant current legislation.

In a further embodiment, the present invention relates to a process for the preparation of a cosmetic composition of the present invention through percolation of ashes and a homogeneous paste of avocado, in alternating layers, in a container that allows outflow of an extractor liquid through the layers, and withdrawal of the percolation product through the bottom of the container. Preferably, the extractor liquid used in percolation of the present invention is water.

The container according to the present invention is preferably a cylindrical container. According to a particular embodiment, such container has a perforated base.

The layers of ashes and avocado paste of the process of this invention are preferably arranged so that the avocado paste layer is between two layers of ashes.

Particularly, the layers are arranged in the container so that ¼ of the total ashes used in the process is placed in the bottom of the container. Such a layer of ashes in the bottom is covered by the total amount of avocado paste that will be, in turn, later covered by the remainder of the ashes.

In the percolation of the present invention, the ashes of the top layer are slowly moistened with water, preferably deionized water. Particularly, the ashes are moistened with water every 3 hours.

The weight ratio of total ashes to total avocado paste utilized is of 1 kg of ashes to about 200 to 300 g of avocado paste. According to a preferred embodiment, 4.5 kg of ashes to 1 kg of avocado paste is used.

The total water used in the percolation process of this invention shall be calculated on the basis of total used ashes, so that about 1 to 1.5 liter of water will be used for each kg of ash, particularly 1.3 liters of water for each kg of ash.

In a preferred embodiment, a total of about 4.5 kg of ashes and about 1 kg of avocado paste is used. This way, the layers arranged in the container are particularly homogeneously and slowly moistened with about 500 ml of deionized water, every 3 hours, up to a total of 6 liters of water.

The percolating product is collected through the holes in the container in a clean bottle.

According to a preferred embodiment, the ashes used in the process of the present invention are obtained from eucalyptus or bracatinga ashes, and are free of coal. Additionally, the avocado paste is preferably obtained from the homogeneous mixture of pulp, peel and stone of avocado with water.

According to the present invention, eucalyptus or bracatinga wood used in order to carry out the procedure described above includes, particularly, pieces of eucalyptus wood of the Eucalyptus globulus species or bracatinga of the Mimosa scrabrela species.

Further, the ashes of the present invention are particularly obtained according to the following steps:

(a) carbonizing eucalyptus or bracatinga logs until obtaining ashes; and (b) sifting the ashes obtained with a sieve, in order to separate the ashes from coal.

In a preferred way, the carbonized wood logs in step (a) comprise approximately from 20 to 40 cm in length and 5 to 15 cm in diameter. Further, the sieve used in step (b) is particularly a sieve of 200 mesh.

More particularly, the carbonized wood logs in step (a) comprise 30 cm in length and 10 cm in diameter.

Eucalyptus ashes contain alkaline and alkaline earth minerals in the presence of carbonates that, when in solution, ensure the property of keeping a high pH. This solution, when applied to the hair strand, acts by disrupting the disulfide bonds, thus enabling the realization of a new hair modeling.

It is known in the prior art that only these ashes in solution are able to shape the hair, however, at the same time, they are aggressive to the hair strand, rendering it weak, opaque and brittle.

This way, through the process of the present invention, it is possible to obtain a cosmetic composition which does not present the drawbacks of a composition containing only the wood ashes.

It was observed in a surprising way that, through the process of the present invention, it is possible to obtain a composition free of formaldehydes, which damage the hair, and, at the same time, to obtain great results of modeling or straightening of keratinous fibers continuously, without damaging the fibers.

The avocado paste used in the process of the present invention is obtained, particularly, from Persea americana avocado.

In a preferred embodiment, the avocado paste of the present invention is particularly obtained according to the following steps:

a) slicing an avocado weighing between approximately 400 to 600 g, comprising pulp and peel;

(b) grinding the avocado slices obtained in (a) in a homogenizer with 500 ml of deionized water until obtaining the homogeneous paste;

(c) grinding the avocado stone separately until obtaining a homogeneous paste;

(d) mixing the pastes obtained in (b) and (c).

The homogeneous avocado paste obtained by the present invention can be stored for about 40 days.

In a further embodiment, the present invention refers to a composition obtained by the process described here and to the use of such composition for straightening and/or modeling keratinous materials, particularly hair.

According to another embodiment, the present invention refers to a cosmetic process for straightening and/or modeling keratinous materials, particularly hair, comprising applying a composition according to the present invention on keratinous materials.

The composition obtained by the process detailed above was tested in different hair types to determine its effectiveness, concentration of use, reaction time and possible adverse effects.

The cosmetic process can be used for any hair type and purpose, and begins with washing the hair with plenty of warm running water and anti-residue shampoo. Then the hair should be dried only with a cotton towel.

Subsequently, the product must be applied only with the hands, about 200 ml, depending on the length of the hair.

The composition obtained in accordance with the present invention requires a resting time of approximately 20 to 40 minutes with hair down without a thermal cap. After this period, the hair can be worked on for straightening or modeling.

The action time of the product on the hair will depend on the characteristics thereof. In fine hair, the reaction time is shorter (about 20 minutes). In the case of frizzy hair, like "afro", the reaction time of the product is longer (about 30 to 40 minutes). The hair type that takes longer for the product to act on is that of Caucasian origin (more than 30 minutes). In all types of hair, it was observed that the product has better action when the hair has no prior chemical treatment, the popular "virgin hair".

The composition of the present invention is compatible with any type of hair treatment existing on the market (formaldehyde, guanidine, dye with ammonia, metallic salts, etc.), and can be applied before or after the process of straightening or modeling. Even after rinsing, the coloring or dyeing can be done without damage to the hair.

An advantage observed with the use of the composition as described in the present invention was the increase in resistance of the hair fiber, since the composition assists in closing the cuticle with a sealing process of the hair.

Another advantage particularly associated with the use of the composition described is that it is not about hydration, but fiber reconstruction as noted in keratin treatments. In addition, the use of the composition of this invention provides increased brightness and softness to the hair.

Another advantage of the use of the composition of the present invention is that in all cases of hair with oily roots, a decrease in oiliness was observed.

An additional advantage associated with the use of the present composition is a decrease in hair loss, especially that caused by oiliness and breaking of hair fiber.

The present invention can be understood more clearly and accurately through reading of the following examples, which illustrate the present invention without any restrictive character.

EXAMPLES

Example 1

Preparation of Raw Material

*Eucalyptus* logs (*Eucalyptus globulus*) of 30 cm in length and 10 cm in diameter were totally carbonized until obtaining ashes. These ashes were sieved to granulometry of 200 mesh and weighted, obtaining a value of approximately 4.5 kg of coal-free ashes.

For this embodiment, bracatinga logs (*Mimosa scrabrella*) can also be used.

Mature avocado (*Persea Americana*), with about 500 g, was sliced (pulp and peel) and grinded in a homogenizer with approximately 500 ml of deionized water until obtaining a completely homogeneous paste. This paste was stored in a 1 liter container.

The avocado stone was also ground separately until forming another paste, which was then mixed with the avocado pulp initially obtained.

Example 2

Preparation Process of Cosmetic Composition

A cylindrical container, perforated at the base, with 30 cm in diameter and 35 cm tall, with a capacity of approximately 25 liters, was used to conduct percolation of the product.

The ashes, as obtained in the example A, were split in four equal parts.

¼ of the total ashes was added in the bottom of the container, lining it in a homogenous way. Then, the avocado paste was spread, mixed with the stone paste, such as obtained in Example A, over the ashes, and the container was filled with the rest of the ashes.

The ashes were moistened with about 500 ml of deionized water homogeneously and slowly, every 3 hours, up to a total of 6 liters of water.

The percolate was collected through the holes in the perforated container into another clean container. This process took about 48 hours, and approximately 2 liters of final product were obtained without pressing the cake.

This percolate can be applied to the clean hair, according to indication, hair type, length, and previous treatment it received.

Example 3

Preparation Process of Cosmetic Composition

In another embodiment, approximately 25% of the total of ashes of *eucalyptus*, as obtained in the example A were placed in the bottom of a 5 liter perforated container.

About 6 liters of water were split in 13 equal parts.

With a portion of the 13 parts of water, a part of the total avocado was ground until a homogeneous paste was formed. This paste was placed on top of the ashes in the perforated container in layers. After filling the layer with all the avocado paste, the other 75% of *eucalyptus* ashes were placed into the container over the avocado paste. Then, the 12-parts of remaining water were added, in-spaced times, for a period of approximately 48 hours.

A percolated product was obtained through the perforations of the container, and this product was collected and stored. At the end of the process, about 2 liters of percolate were obtained and stored in clean plastic bottles.

This percolate can be applied to the clean hair, according to indication, hair type, length, and previous treatment it received.

Example 4

Application of Cosmetic Product

Straightening Process of Hair:

For straightening or relaxing (volume reduction), the hair needs to undergo a process of hairstyling for a period of 20 to 40 minutes. The hair should be washed with shampoo and conditioner.

Process for Making Wavy Hair:

Curl up the curlers and apply about 100 ml of the product on them, and wait approximately 40 minutes. After this time, rinse under running water without releasing the curlers, and then neutralize the hair with any product based on hydrogen peroxide. The hair should be left for another 20 minutes at rest.

After this time, the curlers must be loosened and the hair washed with normal shampoo and conditioner and the process is finished.

As well understood by those skilled in the art, numerous modifications and variations of the present invention are possible in the light of the above teachings, without departing from its scope of protection, as limited by the appended claims.

Example 5

Chemical Analysis of Metals Present in the Composition

Qualitative analysis was performed by x-ray fluorescence (FRX) of inorganic elements (metals) present in: samples of eucalyptus ashes, bracatinga ashes, avocado pulp, peel and stone.

Further, the quantification of the major elements in a sample of the final product by optical emission spectrometry with inductively coupled plasma (ICP OES) or atomic absorption spectrometry was provided.

The used standards are listed in Table 1.

TABLE 1

USED STANDARDS

Standard Solution of Ca 1000 µg/mL brand Accu Standard, Batch B611503-1A
Standard Solution of Fe 1005 µg/mL brand Spec Sol, Batch F12C0333D.
Standard Solution of Mg 1000 µg/mL brand Ultra Scientific, Batch J00348
Standard Solution of Mn 1000 µg/mL brand Accu Standard, Batch B8045178
Standard Solution of Ni 1000 µg/mL brand Accu Standard, Batch B8045143
Standard Solution of K 1001 µg/mL brand Ultra Scientific, Batch J00075
Standard Solution of Na 1000 µg/mL brand Accu Standard, Batch B209065062

Methods of Analysis

X-Ray Fluorescence with Wavelength Dispersion (Qualitative Analysis)

The analysis was performed in FRX spectrometer after preparation of tablets with the samples.

Equipment: Shimadzu XR F1800

Determination of Metals (Quantitative Analysis)

Determinations were performed by ICP OES or by atomic absorption spectrometry using analytic curves built with solutions of the patterns described in table 1.

Equipment:

Plasma Emission Spectrophotometer-ICP, Perkin Elmer 3000 DV;

Atomic Absorption Spectrometer, Analytik Jena NovAA300.

Results

X-Ray Fluorescence (Qualitative Analysis):

In Table 2, metals detected in samples of Eucalyptus, Bracatinga, Pulp, Peel and Stone are listed.

TABLE 2

METALS DETECTED BY X-RAY FLUORESCENCE SPECTROMETRY

| Elements | Eucalyptus | Bracatinga | Pulp | Peel | Stone |
| --- | --- | --- | --- | --- | --- |
| Aluminum | D | D | ND | D | D |
| Barium | ND | D | ND | ND | ND |
| Calcium | D | D | ND | D | D |
| Copper | ND | ND | ND | ND | D |
| Chrome | ND | D | ND | D | ND |
| Strontium | D | D | ND | ND | ND |
| Iron | D | D | ND | D | D |
| Magnesium | D | D | ND | D | D |
| Manganese | D | D | ND | ND | ND |
| Nickel | ND | ND | ND | D | D |
| Potassium | D | D | D | D | D |
| Sodium | D | D | ND | ND | ND |
| Zinc | D | D | ND | ND | ND |

D: Detected;
ND: Non Detected.

The elements that presented the highest percentages in the samples of eucalyptus, bracatinga, pulp, peel and stone were calcium, iron, manganese, nickel, potassium and sodium.

ICP OES and Atomic Absorption Spectrometry (Quantitative Analysis)

For this study, scan was initially conducted in the sample for confirmation of the presence of the metals listed in Table 2 and the absence of some elements was verified. The concentrations of the elements detected are presented in Table 3.

TABLE 3

LEVELS OF CERTAIN METALS IN THE SAMPLE

| | | | Results |
| --- | --- | --- | --- |
| Elements | $LD^2$ | $LQ^3$ | 20 Apr. 2012 |
| Aluminum, mg/L | 0.3 | 0.90 | <LD |
| Barium, mg/L | 0.01 | 0.03 | 0.07 (±0.01) |
| Calcium, mg/L | 2.6 | 8.6 | 20.2 (±0.4) |
| Copper, mg/L | 0.06 | 0.2 | <LD |
| Chrome, mg/L | 0.04 | 0.13 | 0.6 (±0.1) |
| Iron, mg/L | 0.03 | 0.10 | <LQ |
| Manganese, mg/L | 0.5 | 1.5 | <LQ |
| Nickel, mg/L | 0.01 | 0.04 | 0.10 (±0.01) |
| Potassium, % (m/v) | 0.4 | 1.4 | 12.1 (±0.1) |
| Sodium, % (m/v) | 0.1 | 0.3 | 0.15 (±0.01) |

[2]LD: Limit of detection;
[3]LQ:. Limit of quantification.

Example 6

Chemical Analysis of Non-Volatile Compounds Present in the Composition

Qualitative analysis of the sample was performed by gas chromatography with flame ionization detector (GC-FID) and with mass spectrometry (GC/MS).

Methods of Analysis

Determination of Non-Volatiles at 105° C.

The essay was carried out in thermogravimetric scale. 20 mL of each of the samples were heated at 105° C. for 100 minutes.

Equipment: GEHAKA—Termobalanga IV. 2000.

Analysis for Direct Injection into GC-FID and GC-MS

The residues obtained by the determination of non-volatiles at 105° C. were reflowed with methanol and sulfuric acid (trans-esterification by acid catalysis) and subsequently extracted with ethyl ether. The solvent was evaporated and the residue obtained dissolved in dichloromethane for analysis by GC-FID and GC-MS.

Equipment GC-FID: GC-2010 Shimadzu

Equipment GC-MS: Linear quadrupole type mass spectrometer QP-5000 Shimadzu.

Results

The percentage of non-volatile compounds found in composition according to the present invention was of 26 (±1) at 105° C.

GC-FID—Analysis by Direct Injection

A previous study was done with injection into GC-FID to estimate the concentration of organics in the solid fraction obtained by the determination of non-volatiles at 105° C., and it was verified that these compounds are found in trace levels. Thus, to enable a scan of non-volatile organic (qualitative analysis), the sample was pre-concentrated 20 times before injection into GC-MS.

GC-MS—Analysis by Direct Injection

For the identification of the compounds detected in the chromatograms, the database of mass spectra NIST107 and NIST21 was used. When there were significant differences between the mass spectrum obtained and those found in the library, was used the AMDIS program (Automated Mass Spectral Deconvolution Mass & Identification System) for the interpretation of spectra.

Although presented in the chromatograms, the peaks that showed signal to noise ratio of less than 3 or quality index less than 70% were not indicated in the result tables.

The normalized area percentage values (% A) shown in Table 4 indicate only the relative distribution of 25 compounds in the fraction analyzed, i.e. they are not related to masses of total non-volatile fraction or even of the sample.

TABLE 4

COMPOUNDS DETECTED IN THE SAMPLE - ANALYSIS BY DIRECT INJECTION OF THE SAMPLE INTO THE GC/MS.

| #Pitch[1] | $t_R$[2] | Name of compound | % A | Quality |
|---|---|---|---|---|
| 3 | 3.99 | Methoxy Butanol | 3.99 | 76 |
| 4 | 4.75 | Furfural | 9.23 | 77 |
| 6 | 7.30 | Pinene | 5.25 | 90 |
| 8 | 8.42 | Ethyl Hexanol | 2.38 | 81 |
| 11 | 21.48 | Germacreno | 6.95 | 90 |
| 13 | 25.57 | Cyclopentatridecanoic acid | 2.53 | 81 |
| 15 | 27.60 | Dibutil Phthalate | 3.82 | 86 |
| 16 | 28.14 | Hexadecenoic acid | 2.15 | 79 |
| 17 | 28.47 | Hexadecanoic acid (Palmitic acid) | 12.7 | 93 |
| 19 | 29.36 | Ethyl Hexadecanoate | 5.33 | 90 |
| 20 | 29.79 | Methyl Octhyl Phthalate | 4.31 | 73 |
| 21 | 30.31 | Dipenthyl Phthalate | 4.19 | 77 |
| 22 | 30.47 | Mono Octhyl Phthalate | 2.31 | 73 |
| 23 | 30.71 | Octadecanoic acid (Oleic acid) | 2.18 | 79 |
| 24 | 31.0 | Octadecanoic acid | 5.21 | 87 |
| 25 | 31.70 | Ethyl nonadecanoate | 7.69 | 89 |

[1]Number of peak by elution order of the column.
[2]tR = retention time of the compound in the column in minutes.
[3]Most common name of the compound identified.
[4]% A = Percentage of normalized area which indicates the relative distribution of compounds in the sample.
[5]Quality is the search index in the database which reflects the similarity of the mass spectrum obtained with the ones registered in the used libraries. Quality indexes were adopted >70.

All the compounds observed are in trace level, the main identified ones were methoxy butanol, furfural, pinene, germacrene, methylic esthers of fatty acids (palmitic, oleic acid) and phthalates (methyl butyl phthalate, dibutyl phthalate, octyl phthalate and dipentyl phthalate).

As can be observed, some types of phthalates were identified in the sample. These compounds are synthetic plasticizers, widely used in plastic materials. The sample was delivered in plastic bottles, thus, found phthalates are probably from the bottles where the sample was stored in or other plastic material with which the product has been in contact during its production.

Example 7

Chemical Analysis of Volatile Compounds Present in the Composition

A qualitative analysis of volatile organic compounds present in the hair product sample by gas chromatography with flame ionization detector (GC-FID) and mass detector (GC-MS) was provided.

Methods of Analysis

About 5 mL of the sample were transferred to a vial for analysis by headspace. The bottle with the sample was heated at 80° C. for 10 minutes. Then an aliquot of the vapors generated was injected in gas chromatographs with flame ionization and mass detectors.

Equipment:

Gas chromatograph with flame ionization detector-GC-2010 Shimadzu,

Gas chromatograph with mass spectrometer of linear quadrupole type masses—5975C Agilent.

Results

GC-FID—Analysis by Headspace:

The chromatographic profiles suggest that the volatile organic compounds present in the sample are in low concentration levels. This analysis also served to optimize the chromatographic conditions for 20 analysis by GC-MS.

GC-MS—Analysis by Headspace:

For the identification of the compounds detected in the chromatograms the database of mass spectra NIST08 was used. When there were significant differences between the mass spectrum obtained and those found in the library, the AMDIS program (Automated Mass Spectral Deconvolution Mass & Identification System) was used for interpretation of spectra.

The peaks that showed signal to noise ratio of less than 3 or quality index less than 70% were not indicated in the result tables.

The normalized area percentage values (% A) shown in Table 5 indicate only the relative distribution of 5 compounds in the volatile fraction analyzed, i.e. they are not related to masses of total fraction or the sample.

TABLE 5

COMPOUNDS DETECTED IN THE SAMPLE - ANALYSIS BY INJECTION BY HEADSPACE OF THE SAMPLE INTO THE GC-MS.

| # Pitch[1] | $t_R$[2] | Name of the compound[3] | % A[4] | Quality[5] |
|---|---|---|---|---|
| 1 | 19.48 | Dodecamethyl cyclohexasyloxane | 22.18 | AMDIS |
| 2 | 23.87 | Ethoxy hexamethyl Tris(trimetilsyloxy)tetrasyloxane | 16.39 | AMDIS |
| 3 | 32.01 | Buthyl Octhyl Phthalate | 27.06 | AMDIS |
| 4 | 34.29 | Isopropoxy Hexamethyl Tris(trimethylsyloxy)tetrasyloxane | 14.28 | AMDIS |

TABLE 5-continued

COMPOUNDS DETECTED IN THE SAMPLE -
ANALYSIS BY INJECTION BY HEADSPACE
OF THE SAMPLE INTO THE GC-MS.

| # Pitch[1] | $t_R$[2] | Name of the compound[3] | % A[4] | Quality[5] |
|---|---|---|---|---|
| 5 | 37.11 | Buthoxy Hexamethyl Tris(trimethylsyloxy)tetrasyloxane | 16.38 | AMDIS |
| 6 | 39.68 | Not determined | 3.42 | — |

[1]Number of peak by elution order of the column.
[2]tR = Retention time of the compound in the column in minutes.
[3]Most common name of the compound identified.
[4]% A = Percentage of normalized area which indicates the relative distribution of compounds in the sample
[5]Quality is the search index in the database which reflects the similarity of the mass spectrum obtained with the registered in used libraries.

The results obtained allowed the identification of phthalates in the sample. These compounds are synthetic plasticizers, widely used in plastic materials. The sample was delivered in plastic bottles, thus, the found phthalates are probably from the bottles where the sample was stored or other plastic material with which the product has been in contact during its production.

The invention claimed is:

1. A cosmetic composition for straightening or modeling keratinous materials, produced by percolation of an extractor liquid through *eucalyptus* ashes or bracatinga ashes and a homogenous paste of avocado, comprising: i) from 0.001 to 30% of calcium salts; ii) from 1 to 20% of cellulose or derivatives thereof; iii) from 1 to 10% of lignin; iv) from 1 to 10% of fatty acids; v) from 0 to 10% of triglycerides; vi) from 0 to 10% of glycerin; and water.

2. A composition according to claim 1, comprising: i) from 0.001 to 5% of calcium salts; ii) from 1 to 10% of cellulose or derivatives thereof; iii) from 1 to 5% of lignin; iv) from 2 to 6% of fatty acids; v) from 0 to 2% of triglycerides; vi) from 0 to 2% of glycerin; and water.

3. A composition according to claim 2, wherein the keratinous materials are keratinous fibers.

4. A composition according to claim 3, wherein the fatty acids are saturated, monounsaturated and/or polyunsaturated fatty acids.

5. A composition according to claim 4, wherein the fatty acids are oleic, linoleic, stearic and/or palmitic acids.

6. A composition according to claim 5, further comprising siloxane compounds.

7. A process for the preparation of a cosmetic composition comprising percolation of an extractor liquid through ashes and a homogeneous paste of avocado, in alternating layers, in a container that allows outflow of the extractor liquid through the layers and withdrawal of the percolation product through the bottom of the container.

8. A process according to claim 7, wherein the extractor liquid is water.

9. A process according to claim 7, wherein the container is a cylindrical container.

10. A process according to claim 9, wherein the container is a cylindrical container with a perforated base.

11. A process according to claim 10, wherein the alternating layers of ashes and avocado paste are arranged so that the avocado paste layer is between two layers of ashes.

12. A process according to claim 11, wherein ¼ of the total ashes is placed at the bottom of the container and covered by the total amount of avocado paste, which is covered by the remaining of the ashes.

13. A process according to claim 12, wherein the weight ratio between the total ashes and the total avocado paste is 1 kg of ashes to about 200 to 300 g of avocado paste.

14. A process according to claim 13, wherein the weight ratio is about 4.5 kg of ashes and about 1 kg of avocado paste.

15. A process according to claim 13, wherein the ashes of the top layer are slowly moistened with water every 3 hours.

16. A process according to claim 15, wherein about 1 to 1.5 liters of extractor liquid are used for every kg of ashes.

17. A process according to claim 16, wherein a total of about 4.5 kg of ashes and about 1 kg of avocado paste arranged in the container are particularly homogeneously and slowly moistened with about 500 ml of deionized water every 3 hours, up to a total of 6 liters of water.

18. A process according to claim 17, wherein the ashes are obtained from *eucalyptus* or bracatinga, being free of coal.

19. A process according to claim 17, wherein the ashes are obtained by the following steps:
(a) carbonizing *eucalyptus* or bracatinga logs until obtaining ashes; and
(b) sifting the obtained ashes with a sieve in order to separate the ashes from coal.

20. A process according to claim 19, wherein the logs of carbonized wood in step (a) comprise approximately of 20 to 40 cm in length and 5 to 15 cm in diameter.

21. A process according to claim 19, wherein the sieve used in step (b) is a sieve of 200 mesh.

22. A process according to claim 21, wherein the avocado paste is obtained from the homogeneous mixture of avocado pulp, peel and stone with water.

23. A process according to claim 22, wherein the avocado paste is obtained according to the following steps:
(a) slicing an avocado weighing between approximately 400 to 600 g, comprising pulp and peel;
(b) grinding the avocado slices obtained in (a) in a homogenizer with 500 ml of deionized water until obtaining a homogeneous paste;
(c) grinding the avocado stone separately until obtaining a homogeneous paste;
(d) mixing the pastes obtained in (b) and (c).

24. A process according to claim 23, wherein the avocado paste is obtained from *Persea americana* avocado.

25. A cosmetic composition that is obtained through the process as defined in claim 7.

26. A cosmetic process for straightening and/or modeling of keratinous materials, comprising the application of a composition on keratinous materials comprising: i) from 0.001 to 30% of calcium salts; ii) from 1 to 20% of cellulose or derivatives thereof; iii) from 1 to 10% of lignin; iv) from 1 to 10% of fatty acids; v) from 0 to 10% of triglycerides; vi) from 0 to 10% of glycerin; and water, the composition produced by percolation of an extractor liquid through *eucalyptus* ashes or bracatinga ashes and a homogenous paste of avocado.

27. A cosmetic process for straightening and/or modeling of keratinous materials according to claim 26, comprising the application of a composition on keratinous materials, comprising: i) from 0.001 to 5% of calcium salts; ii) from 1 to 10% of cellulose or derivatives thereof; iii) from 1 to 5% of lignin; iv) from 2 to 6% of fatty acids; v) from 0 to 2% of triglycerides; vi) from 0 to 2% of glycerin; and water.

28. A process according to claim 26 wherein the keratinous materials are keratinous fibers.

29. A process according to claim 28 wherein the keratinous fibers are hair.

30. A composition according to claim 3 wherein the keratinous fibers are hair.

31. A process according to claim 15, wherein the water is deionized water.

32. A composition according to claim 2 comprising i) 0.002% of calcium salts; ii) 6.6% of cellulose or derivatives thereof; iii) 1.2% of lignin; iv) 4.8% of fatty acids; and water.

33. A composition according to claim 1 wherein the ashes are free of coal.

34. A composition according to claim 1, wherein the extractor liquid is water.

* * * * *